United States Patent [19]

Eberle et al.

[11] 4,054,665

[45] Oct. 18, 1977

[54] 2-AMINO-5-(TRIFLUOROMETHYL-PHENYLALKYL)-1,3,4 THIADIAZOLES USED IN THE TREATMENT OF INSOMNIA AND ANXIETY

[75] Inventors: Marcel K. Eberle, Madison; Robert E. Manning, Mountain Lakes, both of N.J.

[73] Assignee: Sandoz, Inc., Hanover, N.J.

[21] Appl. No.: 665,776

[22] Filed: Mar. 10, 1976

Related U.S. Application Data

[60] Division of Ser. No. 528,477, Nov. 29, 1974, Pat. No. 3,965,110, which is a continuation-in-part of Ser. No. 485,991, July 5, 1974, abandoned, which is a continuation-in-part of Ser. No. 452,678, March 20, 1974, abandoned, which is a continuation-in-part of Ser. No. 218,559, Jan. 17, 1972, abandoned, which is a continuation-in-part of Ser. No. 124,489, March 15, 1971, abandoned.

[51] Int. Cl.$^2$ ........................................... A61K 31/425
[52] U.S. Cl. .................................................. 424/270
[58] Field of Search ................. 424/270; 260/306.8 D

[56] References Cited

U.S. PATENT DOCUMENTS

| 3,746,716 | 7/1973 | Tweit | 260/306.8 D |
|---|---|---|---|
| 3,965,110 | 6/1976 | Eberle et al. | 260/306.8 D |

*Primary Examiner*—Leonard Schenkman
*Attorney, Agent, or Firm*—Gerald D. Sharkin; Robert S. Honor; Timothy G. Rothwell

[57] ABSTRACT

2-amino-5-(substituted or unsubstituted phenylalkyl)-1,3,4-thiadiazoles, e.g., 2-amino-5-(3-trifluoromethylbenzyl)-1,3,4-thiadiazole, prepared, e.g., by ring closure, of corresponding 1-(substituted or unsubstituted phenylalkanoyl)-thiosemicarbazide in a strong acid medium. The compounds are useful as minor tranquilizers and sleep inducers.

3 Claims, No Drawings

2-AMINO-5-(TRIFLUOROMETHYLPHENYLALK-YL)-1,3,4 THIADIAZOLES USED IN THE TREATMENT OF INSOMNIA AND ANXIETY

This application is a division of copending application Ser. No. 528,477 filed Nov. 29, 1974 which issued as U.S. Pat. No. 3,965,110 on June 22, 1976 which in turn is a continuation-in-part of copending application Ser. No. 485,991 filed July 5, 1974, now abandoned, which in turn is a continuation-in-part of copending application Ser. No. 452,678, filed Mar. 20, 1974, now abandoned, which in turn is a continuation-in-part of application Ser. No. 218,559, filed Jan. 17, 1972, now abandoned, which in turn is a continuation-in-part of application Ser. No. 124,489, filed Mar. 15, 1971, now abandoned.

This invention relates to 2,5-substituted 1,3,4-thiadiazoles. More particularly, it relates to 2-amino-5-(substituted or unsubstituted phenylalkyl)-1,3,4-thiadiazoles, intermediates thereof to processes for their preparation, and pharmaceutically acceptable acid addition salts.

The compounds of this invention may be represented by the following structural formula:

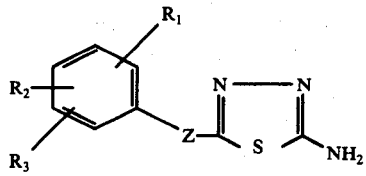

(I)

where
$R_1$, $R_2$ and $R_3$ each independently represent hydrogen, halo having an atomic weight of about 19 to 36 or trifluoromethyl, and
Z is — $(CH_2)_n$—, $$-\overset{R_4}{\underset{|}{HC}}-(CH_2)_m- \quad \text{or} \quad -(CH_2)_p-\overset{R_4}{\underset{|}{CH}}-$$

where
$R_4$ is lower alkyl having 1 to 4 carbon atoms, e.g., methyl, ethyl, isopropyl, and the like, and
$n$ is 1, 2, 3, or 4, and
$m$ is 0, 1, 2, or 3, and
$p$ is 1, 2 or 3,
provided that (a) at least one of $R_1$, $R_2$, and $R_3$ is trifluoromethyl, and (b) that when more than one of $R_1$, $R_2$, and $R_3$ is trifluoromethyl, they are bonded to other than adjacent carbon atoms and (c) where two of the substituents are trifluoromethyl, the remaining substituent is hydrogen.

The compounds of formula (I) may also be represented by the following structural formulae:

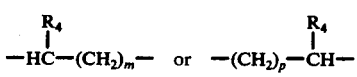

(Ia)

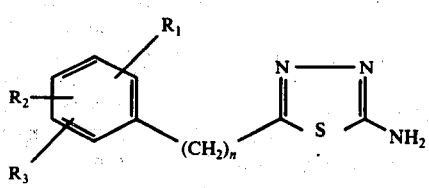

(Ib)

-continued

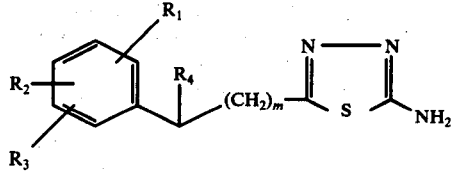

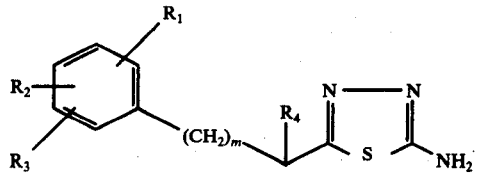

(Ic)

wherein $R_1$, $R_2$, $R_3$, $R_4$, m, n and the proviso have the above stated significance.

The compounds of formula (I) may be prepared by the following reaction scheme A:

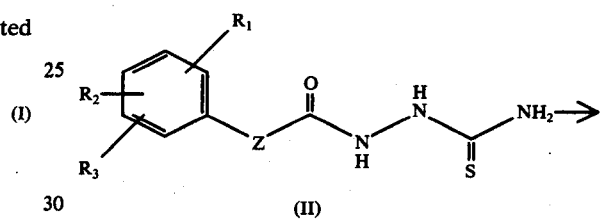

(II)

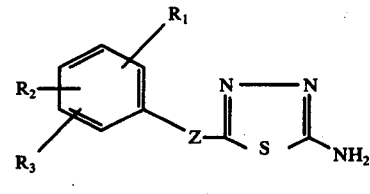

(I)

wherein $R_1$, $R_2$, $R_3$, Z and the proviso have the above stated significance.

The compounds of formula (I) may be prepared by the following reactions scheme A:

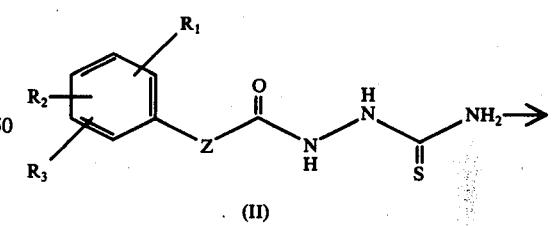

(II)

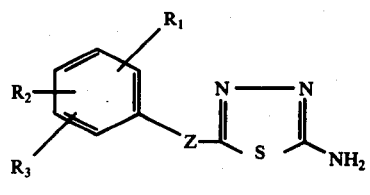

(I)

wherein $R_1$, $R_2$, $R_3$, Z and the proviso have the above stated significance.

The compounds of formula (I) may be prepared by ring closure of a compound of formula (II) in a strong Lewis acid medium such as phosphoric acid, hydrochloric acid, sulfuric acid, and the like, or a halogenated phosphoric acid, such as phosphorous tribromide, at a temperature of from 40° to 100° C., preferably 50° to 65° C. for about 0.5 to 20 hours, preferably 2 to 6 hours. Though a solvent is not necessary, inert aromatic solvents such as benzene, toluene, xylene, chlorobenzene and the like may be used. Neither the temperatures nor the times used are critical.

The compounds of formula (I) may also be prepared by the following reaction scheme B:

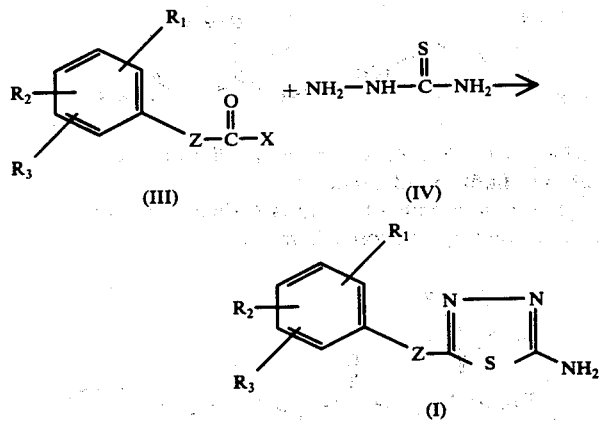

wherein X is halo having an atomic weight of 35 to 80, and $R_1$, $R_2$, $R_3$, Z and the proviso have the above stated significance.

The compounds of formula (I) may be prepared by treating a substituted or unsubstituted phenylalkanoylhalide, e.g., m-trifluoromethylphenylacetylchloride, with thiosemicarbazide in a strong Lewis acid medium such as described respecting scheme A, at a temperature of from 40° to 100° C., preferably 50° to 65° C. for about 0.5 to 20 hours, preferably about 2 to 6 hours. Though a solvent is not necessary, inert solvents such as described respecting scheme A may be used if desired. Neither the temperatures nor the times used are critical.

The compounds of formula (II) may be prepared by the following reaction scheme C:

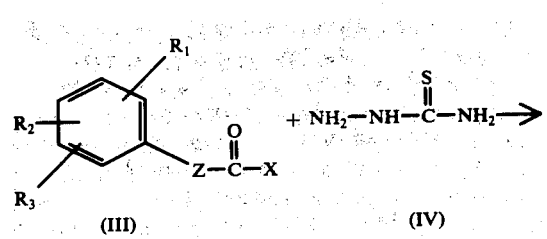

wherein $R_1$, $R_2$, $R_3$, Z, X and the proviso have the above stated significance.

The compounds of formula (II) may be prepared by treating a compound of formula (III) with thiosemicarbazide in an inert solvent such as dialkylformamide, e.g., dimethylformamide, at a temperature of from 0° to 80° C., preferably 15° to 50° C., for about 1 to 24 hours, preferably 2 to 6 hours. Neither the solvents nor the temperature or time used is critical.

The compounds of formula (II) may also be prepared by the following reaction scheme D:

wherein $R_5$ is lower alkyl as defined above, and $R_1$, $R_2$, $R_3$, Z and X have the above stated significance.

The compounds of formula (II) may be prepared in the first step by treating a compound of formula (III) with an excess of hydrazine (VI) in an inert solvent such as the ethers, e.g., methylether, diethylether, and the like, or the aromatic hydrocarbons, such as benzene, toluene, and the like, optionally in the presence of an alkali metal carbonate, e.g., potassium carbonate, sodium carbonate, and the like, preferably sodium carbonate, at a temperature of from 20° C. to the reflux temperature of the solvent, preferable at room temperature for about 1 to 8 hours, preferably 3 to 5 hours, to give the intermediate compound (VII). In the second step, compound (VII) is dissolved in concentrated hydrochloric acid or concentrated sulfuric acid and treated with an excess of potassium thioisocyanate (VIII) at the reflux temperature of the aqueous acid medium for about 1 to 8 hours, preferably 3 to 5 hours. Neither the temperatures nor the times used are critical.

The compounds of formula (II) may alternatively be prepared by treating a compound of formula (V) in the first step with an excess of hydrazine (VI) in an aqueous or inert solvent such as lower alkanols having 1 to 4 carbon atoms, e.g., methanol, ethanol and the like, benzene, toluene, and the like, at a temperature of from 0° to 120° C., preferably at reflux temperature of the solvent for 1 to 4 hours, preferably 1 to 2 hours, to give the intermediate compounds (VII). Compound (VII) is then treated as described in step two above. Neither the temperature nor the time used is critical.

The compounds of formulae (I) and (II) may be recovered by conventional recover techniques such as crystallization.

Certain of the compounds of formulae (III), (IV), (V), and (VII) are known and may be prepared by methods disclosed in the literature. These compounds of formulae (III), (IV), (V), and (VII) not specifically disclosed may be prepared according to analogous methods from known materials.

The compounds of formula (I) are useful because they possess pharmacological activity. In particular, the compounds are useful as central nervous system depressants, especially as sedative-hypnotics and minor tranquilizers as indicated by (1) their ability to produce docility in behavior tests in mice given 25 to 200 mg/kg of animal body weight, i.p. of the test compound according to the 30-word adjective check sheet system basically as described by Irwin S. Gordon (Research Conference, Medicinal Chemistry, 1959) and Chen (Symposium on Sedative and Hypnotic Drugs, Williams and Wilkins, 1954); (2) by their ability to antagonize chronic convulsions and death in mice given 50 to 250 mg/kg i.p. of N-sulfamoylazepine; (3) by the hexobarbital reinduction method of Winter, (J. Pharmacol and Exp. Therap., 94, 7–11 1948) in which the reinduction of anesthesia after recovery from hexobarbital induced anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; (4) as indicated in Cebus monkey using chlonically implanted electrodes. Brain readings are obtained via a 10 or 16 channel electroencephalograph. For the recording sessions, the monkeys are restrained by neck and waist plates in chairs in full side observation cages at the same time every night for 13½ hours Monday through Thursday. Gross behavior is monitored via closed circuit television and video tape recordings. The compounds of formula (I) are administered p.o. at a dosage of from about 1.8 to about 30 mg/kg immediately on placing the monkey in the observation cages with at least 7 days intervening between drug administration. Physiological saline is administered via a similar route and at the same times on all control runs. Control data are collected at least 3 days per week and accumulated to give control data for 15 sessions per monkey. Data from each session are statistically compared via computer analysis to the previous 5–15 control sessions for the particular animal, with particular emphasis given to the following phases of the sleep-wakefulness cycle: resting awake, light sleep, deep sleep, paradoxical (REM) sleep, "pseudo-" paradoxical sleep, latency to onset of deep sleep, and latency to onset of first epoch of paradoxical sleep; and (5) as indicated in the cat given typically 5 to 30 mg/kg of animal body weight of the active material and tested in sleep studies using chronic cortical and subcortical electrode placements, with eye movement measured via electrooculogram. Brain readings are obtained via Gross Model 6 electroencephalographs, and the gross behavior of the animal is monitored via closed circuit television and video tape recordings.

For such usage, the compounds may be administered orally or parenterally as such or admixed with conventional pharmaceutical carriers.

The dosage of active ingredient employed for minor tranquilizer use may vary depending on the severity of the condition being treated. However, in general, satisfactory results are obtained when a compound of formula (I) is administered at a daily dosage of from about 1 milligram to about 150 milligrams per kilogram of animal body weight p.o., preferably given in divided does 2 to 4 times a day, or in sustained release form. For most larger mammals (e.g., primates) the total daily dosage is from about 75 milligrams to about 1500 milligrams. Dosage forms suitable for internal use comprise from about 18 to about 750 milligrams of active compound in intimate admixture with a solid or liquid pharmaceutically acceptable carrier or diluent.

The dosage of activated ingredient employed for sedative-hypnotic use may vary depending on the severity of the condition being treated. However, in general, satisfactory results are obtained when a compound of the formula (I) is administered at a daily dosage of from about 1 milligram to about 150 milligrams per kilogram of animal body weight p.o., typically given in a single dose at bedtime. For most larger mammals, the total daily dosage is from about 75 milligrams to about 1500 milligrams, preferably at bedtime in a single dose.

Furthermore, the compounds of formula (I) may be similarly administered in the form of their non-toxic, pharmaceutically acceptable acid additon salts. Such salts possess the same order of activity as the free base and are readily prepared by reacting the base with an appropriate acid and, accordingly, are included within the scope of the invention. Representative of the acid addition salts are the mineral acid salts, such as the hydrochloride, hydrobromide, sulfate, phosphate and the like, and the organic acid salts, such as succinate, benzoate, acetate, p-toluenesulfonate, benzenesulfonate and the like.

EXAMPLE 1

3-trifluoromethylphenylacetyl-3-thiosemicarbazide

A mixture of 60.0 g. (0.3 mole) of 3-trifluoromethylphenylacetic acid and 80 ml. of thionyl chloride in the presence of 10 drops of dimethylformamide is heated on a water bath for 3 hours. The excess thionyl chloride is evaporated under reduced pressure, and any remaining traces of thionyl chloride are removed by adding dry benzene followed by evaporation. To the resulting acid chloride dissolved in 100 ml. of absolute dimethylformamide is added with cooling 29.3 g. (0.32 mole) of thiosemicarbazide. The mixture is maintained at room temperature overnight and the excess solvent is removed under reduced pressure. To the resulting residue there is added ice water to precipitate a solid which is then recrystallized from acetane/hexane to give 3 -trifluoromethylphenylacetyl-3-thiosemicarbazide, m.p. 197°–199° C.

Following the above procedure and using in place of 3-trifluoromethylphenylacetic acid, an equivalent amount of a. 4-trifluoromethylphenylacetic acid,
b. 3,5-trifluoromethylphenylacetic acid,
c. 5-chloro-3-trifluoromethylphenylacetic acid,
d. 2,5-dichloro-3-trifluoromethylphenylacetic acid,
e. 3-trifluoromethylphenylpropionic acid,
f. 3-trifluoromethylphenylbutyric acid,
g. 3-trifluoromethylphenylpentanoic acid,
h. 2-(3-trifluoromethylphenyl)-propionic acid,
i. 3-(3-trifluoromethylphenyl)-butyric acid,
j. 4-(3-trifluoromethylphenyl)-pentanoic acid, or
k. 2-methyl-3-(3-trifluoromethylphenyl)-acetic acid, there is obtained a. 4'-trifluoromethylphenylacetyl-3-thiosemicarbazide,
b. 3',5'-trifluoromethylphenylacetyl-3-thiosemicarbazide,
c. 5'-chloro-3'-trifluoromethylphenylacetyl-3-thiosemicarbazide,
d. 2',5'-dichloro-3'-trifluoromethylphenylacetyl-3-thiosemicarbazide,
e. 3'-trifluoromethylphenylpropionyl-3-thiosemicarbazide,
f. 3'-trifluoromethylphenylbutyryl-3-thiosemicarbazide,
g. 3'-trifluoromethylphenylpentanoyl-3-thiosemicarbazide,
h. 3-(2-[3-trifluoromethylphenyl]-propionyl)-thiosemicarbazide,
i. 3-(3-[3-trifluoromethylphenyl]-butryl)-thiosemicarbazide,
j. 3-(4-[3-trifluoromethylphenyl]-pentanoyl)-thiosemicarbazide, or
k. 3-(2-methyl-3-[3-trifluoromethylphenyl]-propionyl)-thiosemicarbazide, respectively.

EXAMPLE 2

2-amino-5-(3-trifluoromethylbenzyl)-1,3,5-thiadiazole

A mixture of 32.0 g. (0.115 mole) of 3'-trifluoromethylphenylacetyl-3-thiosemicarbazide and 48.0 g. of phosphorous tribromide is heated in a waterbath to a temperature of 60°–65° C. and maintained for 4 hours. The resulting mixture is cooled and poured onto a 50% solution of sodium hydroxide in ice water. The resulting product is extracted using methylene chloride, washed with water and dried over potassium carbonate. The excess solvent is evaporated and the resulting product recrystallized from methanol and water to give 2-amino-5-(3-trifluoromethylbenzyl)-1,3,4-thiadiazole, m.p. 174°–176° C.

Following the above procedure and using in place of 3'-trifluoromethylphenylacetyl-3-thiosemicarbazide, an equivalent amount of a. 4'-trifluoromethylphenylacetyl-3-thiosemicarbazide,
b. 3',5'-trifluoromethylphenylacetyl-3-thiosemicarbazide,
c. 5'-chloro-3'-trifluoromethylphenylacetyl-3-thiosemicarbazide,
d. 2',5'-dichloro-3'-trifluoromethylphenylacetyl-3-thiosemicarbazide,
e. 3'-trifluoromethylphenylpropionyl-3-thiosemicarbazide,
f. 3'-trifluoromethylphenylbutyryl-3-thiosemicarbazide,
g. 3'-trifluoromethylphenylpentanoyl-3-thiosemicarbazide,
h. 3-(2-[3-trifluoromethylphenyl]-propionyl-thiosemicarbazide,
i. 3-(3-[3-trifluoromethylphenyl]-butryl)-thiosemicarbazide,
j. 3-(4-[3-trifluoromethylphenyl]-pentanoyl)-thiosemicarbazide, or
k. 3-(2-methyl-3-[3-trifluoromethylphenyl]-propionyl)-thiosemicarbazide, there is obtained a. 2-amino-5-(4-trifluoromethylbenzyl)-1,3,4-thiadiazole,
b. 2-amino-5-(3,5-ditrifluoromethylbenzyl)-1,3,4-thiadiazole,
c. 2-amino-5-(5-chloro-3-trifluoromethylbenzyl)-1,3,4-thiadiazole,
d. 2-amino-5-(2,5-dichloro-3-trifluoromethylbenzyl)-1,3,4-thiadiazole,
e. 2-amino-5-(3-trifluoromethylphenethyl)-1,3,4-thiadiazole,
f. 2-amino-5-(3-trifluoromethylphenylpropyl)-1,3,4-thiadiazole,
g. 2-amino-5-(3-trifluoromethylphenylbutyl)-1,3,4-thiadiazole,
h. 2-amino-5-(2-[3-trifluoromethylphenyl]-ethyl)-1,3,4-thiadiazole,
i. 2-amino-5-(3-[3-trifluoromethylphenyl]-propyl)-1,3,4-thiadiazole,
j. 2-amino-5-(4-[3-trifluoromethylphenyl]-butyl)-1,3,4-thiadiazole, or
k. 2-amino-5-(1-methyl-2-[3-trifluoromethylphenyl]-ethyl)-1,3,4-thiadiazole, respectively.

It will be appreciated that the final compounds of Example 2 may exist in hydrochloride salt form and may be prepared employing conventional techniques and are included within the scope of this invention.

What is claimed is:

1. A pharmaceutical composition for use in treating insomnia or anxiety comprising a therapeutically effective amount of a compound of the formula

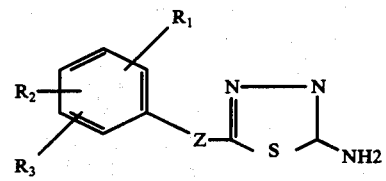

where
$R_1$, $R_2$, and $R_3$ each independently represent hydrogen, fluoro, chloro, or trifluoromethyl, and
Z is — $(CH_2)_n$—,

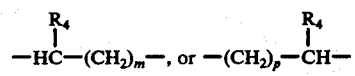

where
$R_4$ is lower alkyl, and
$n$ is 1, 2, 3, or 4, and
$m$ is 0, 1, 2, or 3, and
$p$ is 1, 2, or 3,
provided that (a) at least one of $R_1$, $R_2$, and $R_3$ is trifluoromethyl, and (b) that when more than one of $R_1$, $R_2$, and $R_3$ is trifluoromethyl, they are bonded to other than adjacent carbon atoms and (c) where two of the substituents are trifluoromethyl, the remaining substituent is hydrogen, in association with a pharmaceutically acceptable carrier therefor.

2. A method of treating insomnia, which comprises administering to a mammal in need of said treatment an effective amount of a compound of the formula

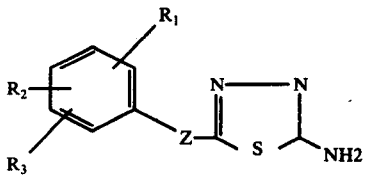

where
$R_1$, $R_2$, and $R_3$ each independently represent hydrogen, fluoro, chloro, or trifluoromethyl, and
Z is $-(CH_2)_n-$,

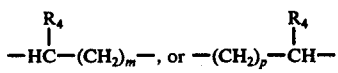

where
$R_4$ is lower alkyl, and
$n$ is 1, 2, 3, or 4, and
$m$ is 0, 1, 2, or 3, and
$p$ is 1, 2, or 3,
provided that (a) at least one of $R_1$, $R_2$, and $R_3$ is trifluoromethyl, and (b) that when more than one of $R_1$, $R_2$, and $R_3$ is trifluoromethyl, they are bonded to other than adjacent carbon atoms and (c) where two of the substituents are trifluoromethyl, the remaining substituent is hydrogen.

3. A method of treating anxiety, which comprises administering to a mammal in need of said treatment an effective amount of a compound of the formula

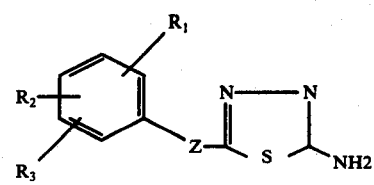

where
$R_1$, $R_2$, and $R_3$ each independently represent hydrogen, fluoro, chloro, or trifluoromethyl, and
Z is $-(CH_2)_n-$,

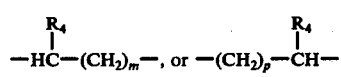

where
$R_4$ is lower alkyl, and
$n$ is 1, 2, 3, or 4, and
$m$ is 0, 1, 2, or 3, and
$p$ is 1, 2, or 3,
provided that (a) at least one of $R_1$, $R_2$, and $R_3$ is trifluoromethyl, and (b) that when more than one of $R_1$, $R_2$, and $R_3$ is trifluoromethyl, they are bonded to other than adjacent carbon atoms and (c) where two of the substituents are trifluoromethyl, the remaining substituent is hydrogen.

* * * * *